United States Patent [19]
Grim et al.

[11] Patent Number: 4,996,979
[45] Date of Patent: * Mar. 5, 1991

[54] SOFT-GOODS TYPE, FORMABLE ORTHOPAEDIC CAST

[75] Inventors: Tracy E. Grim, Broken Arrow, Okla.; Vincent McGinniss, Sunbury, Ohio; Kenneth E. Hughes, Gahanna, Ohio; David A. Easter, Westerville, Ohio; Robert S. Whitmore, Jr.; Timothy J. Carpenter, both of Columbus, Ohio; David E. Guza, Dublin, Ohio

[73] Assignee: Royce Medical Company, Westlake Village, Calif.

[*] Notice: The portion of the term of this patent subsequent to May 29, 2007 has been disclaimed.

[21] Appl. No.: 420,920

[22] Filed: Oct. 13, 1989

[51] Int. Cl.$^5$ .............................. A61F 5/04; A61F 5/31
[52] U.S. Cl. ................................. 128/89 R; 128/878; 128/90
[58] Field of Search ................. 128/89 R, 87 R, 91 R, 128/877, 878, 90, 91 A, 77, 165, 881, 882, 846, 847, 88, 879

[56] References Cited

U.S. PATENT DOCUMENTS

| | | | |
|---|---|---|---|
| 3,373,741 | 3/1968 | Hill | 128/90 |
| 4,300,542 | 11/1981 | Baron | 128/DIG. 20 |
| 4,483,332 | 11/1984 | Rind | 128/90 |
| 4,537,184 | 8/1985 | Williams, Jr. | 128/90 |
| 4,683,877 | 8/1987 | Ersfeld | 128/90 |
| 4,852,557 | 8/1989 | Grim | 128/88 |
| 4,928,678 | 5/1990 | Grim | 128/878 |

Primary Examiner—Robert A. Hafer
Assistant Examiner—Michael Brown
Attorney, Agent, or Firm—Poms, Smith, Lande & Rose

[57] ABSTRACT

A soft goods type foldable, wrappable sleeve orthopedic cast immobilizes and conforms to the shape and configuration of a limb, or other part of the anatomy. The soft-goods type cast assembly is initially specially formed or configured to specifically fit a selected portion of the anatomy of a patient. The cast conforms to the anatomy through the use of airtight and moisture-proof pouches which encapsulate either (1) open cell or fiberglass matrices impregnated with a water-activated hardenable pre-polymer, or (2) the entire assembly. After the tightening of the cast around the limb, the application of water activates the urethane polymer which conforms to the configuration of the limb encased. Supplemental bendable ribs may be employed to splint the limb prior to activation of the hardenable material. The soft goods type cast is held in place by straps, and may be removed or adjusted by releasing or tightening the straps. The splinting elements may be removed and replaced. An inlet duct may have a capsule in it with some of the chemical material which aids in polymerization of the urethane. A venting duct may also be provided to permit the escape of air or gases. The water activated pre-polymer material may include two isocyanate pre-polymers of significantly different viscosities and equivalent weights.

26 Claims, 6 Drawing Sheets

SOFT-GOODS TYPE, FORMABLE ORTHOPAEDIC CAST

RELATED PATENT APPLICATIONS

This patent application is related to U.S. patent application Ser. No. 198,152, filed May 24, 1988, and assigned to the assignee of the present application.

FIELD OF INVENTION

This invention relates to methods of immobilizing body limbs or joints by using a lightweight, formable orthopaedic cast splint system.

BACKGROUND OF THE INVENTION

The traditional orthopaedic cast used bandages loaded with plaster of paris, which was then wrapped around the body limb which was injured or broken. The traditional plaster of paris cast is bulky, weighty and very uncomfortable for the wearer. Many techniques and systems have been proposed to either cut down on the weight, decrease the bulkiness or improve the comfort for the user. In addition, attempts have been made to design and make portable casts which are to be used at the site of an accident for quick reaction to injuries. Certain casts and systems of this type are set forth in U.S. Pat. Nos. 3,375,822; 3,643,656; 4,483,332; 4,537,147, and 4,683,877. While in whole or in part these patented orthopedic cast systems have claimed lightweight or portability or an improved method as compared with plaster of paris casts, in fact, many have not lived up to their promise. In the cases noted above it appears that these cited references herein have reduced weight, but not improved comfort, or in many instances ease of use has been sacrificed. Also, none present the opportunity to remove the cast during use for cleansing the body limb, for comfort, and for improved X-ray examination.

Accordingly, principal objectives of the present invention are to provide an orthopedic cast and splint system which is lightweight, formable to the anatomy, and removable for ease of use. In accomplishing those needs, the invention will also increase the immobilization and stability of the limb or other portion of the anatomy to ensure the prevention of unneeded movements which could complicate healing.

Further objects of the invention are to increase the shelf life of soft-goods, type formable casts, and to provide flexibility in the use of such casts.

SUMMARY OF THE INVENTION

The present invention involves a new and improved orthopedic cast which is foldable or wrappable and lightweight, which conforms to the unique configuration of an individualized limb, or other portion of the anatomy, and which is adjustable to accommodate limb swelling and muscle atrophy variations. The orthopedic cast has on its exterior surface or within the foam padding of its parallel material layers, a single or a plurality of formable pouches which encapsulate a water-activatable urethane impregnated matrix, formed of material such as an open cell foam, honeycomb material, fiberglass, Kevlar, carbonaceous fibers, or similar materials. The pouch encloses unpolymerized urethane, or other hardenable material, which only begins polymerization and hardening upon the introduction of water or other activation chemistry. Alternatively, a water and gas impermeable pouch may encompass the entire soft-goods type formable cast assembly.

In one aspect of the invention, the orthopaedic cast is similar to a soft goods type orthopaedic brace, including padding and straps for securing it to a limb or a joint. In addition, the cast has at least one elongated airtight pouch containing water-activated, hardenable material, such as urethane, in an open cell foam or in a fibrous matrix, and arrangements for applying the water to reach and activate the entire urethane impregnated material.

Alternatively, the air and moisture tight pouch may enclose the entire soft-goods unit, and the water-activated hardenable material may be enclosed in a water-permeable pouch so that when the soft-goods type cast is to be used the outer waterproof packaging is opened, and water is applied to the hardenable material, as the unit is applied to the patient.

The cast may be wrapped around a limb, for example, an arm. The cast surrounds the arm and through a securing fastening system, constrains and immobilizes the arm. The injury to the arm such as a break or severe sprain would need such immobilization to heal. As the wrappable, foldable and lightweight sleeve is secured around the limb, the airtight pouches can initially conform to the limb configuration, with bendable splint ribs to initially conform and immobilize the limb. Upon the secure tightening of the cast, and the contacting of water with the hardenable material, the urethane prepolymer will polymerize, harden and conform to the limb. While the time for applying the water to the hardenable material does not have to be immediately after the cast's application, it is contemplated that such application would be within minutes of the setting of the injured limb and its immobilization within the cast.

The polymerization of the urethane improves the stability of the limb-case combination and prevents any movement which would interfere with healing. Upon the occurrence of an injury, the injured limb would be set and wrapped in the cast. The cast would be firmly secured about the limb, preferably with the use of strapping and Velcro pads. Upon completion of the cast's sleeve being tightly secured about the limb, each plastic foil pouch may have a predetermined amount of water injected by a syringe or other suitable technique. It is contemplated that each pouch or cast assembly could have a syringe associated with it for containing the amount of water necessary for polymerization. The syringe device could be for a one time use. With the syringe containing the necessary quantity of water, there would be no need for measuring the necessary water, which could result in too much or too little water being injected. Alternatively, when the entire unit is enclosed within a moisture-proof pouch, water may be applied either before or after securing the soft-goods type splint to the patient.

The pouches themselves should be airtight and moisture-proof, and may be constructed of multiple layers of materials, typically layers of plastic and metallic foil. These combinations would make the pouches structurally strong as well as gas and moisture impermeable, with the plastic providing the strength and the foils being airtight. Certain known flexible plastic materials are also airtight and moisture-proof, and they could be used alone without the supplemental metal foil.

In the case of certain embodiments, within the pouches would be one or more substrates or matrices impregnated with the water-activatable urethane polymer. Arrangements are provided for distributing the water from the inlet port to saturate and activate the entire matrix which is impregnated with the water activated hardenable material. This may be accomplished through the use of a distribution manifold or plenum separated by a perforated plastic sheet from the matrix, and with the sheet closer to the matrix and having larger holes, and a higher density of holes, away from the inlet port, as compared with near the port. Alternatively, a tree type distribution channel with a series of branching channels may be provided.

The water may be delivered into the pouch cavity by means of an inlet which may include a one-way valve. The water may contact the perforated plastic surface at a planar level closest to the inlet opening, and flows through the distribution volume, and the water then contacts the impregnated substrate or matrix initiating polymerization, by means of the holes in the plastic sheet. The holes in the plane closest to the water entry port are the smallest and the openings remote from the entry port and closest to the substrate surface are the largest. This arrangement is to ensure that water flows and contacts the substrate in a uniform manner. Alternatively, there could be a water delivery system wherein the entry port is coupled to tubes which break out in a tree fashion incorporated within the pouch so that small tubes extend to all areas of the matrix to ensure uniform contact with the impregnated matrix.

In accordance with additional aspects of the invention, the cast may be provided with bendable splint ribs of aluminum or plastic for initial holding of the limb while the water-activated hardenable material is being set up. It is also desirable that the pouches be maintained free of moisture, and this may be accomplished by manufacture in a dry environment, or by back-filling the airtight pouches with an inert gas, such as nitrogen. It is also noted that it is desirable that the cast systems be adjustable and removable, preferably by having hinge lines in the cast or using flexible sections of the soft goods assembly, and by the use of straps having Velcro securing arrangements. Further, both the pouches and the bendable splinting members may be mounted in removably closed elongated pockets in the soft goods cast assembly, so they may be removed and replaced as desired. The inlet port may have a threaded cap for resealing, and may be provided with a one-way valve. Alternatively, an input membrane may be used, with water being injected through the membrane by the needle of a medical syringe or the like.

In accordance with another aspect of the invention, the soft-goods type, formable orthopaedic cast may have special configurations applicable to any desired portion of the anatomy, such as the forearm, the leg, or the thumb, for specific examples.

In accordance with a further aspect of the invention, the inner structure of the unit in which the hardenable material is found may be provided with an input duct through which water and/or other chemical substances are supplied, and a venting duct for the escape of air or other vapors as fluid is supplied through the input duct.

In accordance with yet another aspect of the invention, some portion of the chemistry, such as a catalyst, or co-reactant, useful in the activation and hardening of the urethane or other hardenable material, may be isolated in a capsule in the water inlet duct or tube, or in multiple capsules or a thin enclosed layer within or adjacent to the hardenable material. The capsule wall or outer layer may be formed of a water-soluble material, such as polyvinyl alcohol, so that it dissolves promptly when engaged by the incoming water, and the chemical substance enclosed in the capsule is carried in to polymerize the impregnated material to initiate the hardening step in the solution provided by the incoming water. By separating or isolating one of the chemical components, by water soluble capsules or layers, the possibility of premature activation of the hardening step is reduced, and the expected shelf life of the product may be extended.

Another feature of the invention involves the optional use of a special water-absorbing substance to absorb excess water following application of water to the activatable hardenable material. One such material which may be employed is a hydrogel, and another is a modified starch sold under the trademark "Superslurper". It is further noted that this water absorbing material may extend in a layer, between two layers of hardenable material to initially draw water to the inner surfaces of the hardenable material, and to absorb the excess water following full activation by water of the hardenable material.

It is further noted that one preferred assembly would include an inner layer of tricot or brushed nylon to engage the patient's skin, a thin layer of foam, and then a sealed pouch. Within the sealed pouch is a perforated pouch enclosing a laminated structure including high strength material such as KEVLAR or or fiberglass, and one or more inner layers of open-celled foam or other porous material impregnated with hardenable material. The inlet and vent ducts may extend into the sealed pouch; and an outer layer of foam may cover the pouch, with a final outer layer of vinyl, brushed nylon, or other similar material enclosing the assembly.

As a further aspect of the invention, the use of two different isocyanate pre-polymers, one of relatively low viscosity and equivalent weight, and the other of relatively high viscosity and equivalent weight, is preferred as producing a quick setting, high strength splint. The low viscosity pre-polymer has a viscosity below 500 centipoise, and preferably below 200 centipoise; while the high viscosity pre-polymer has a viscosity above 1,000 centipoise, and preferably above 4,000 centipoise.

Other objects, features and advantages of the invention will become apparent from a consideration of the following detailed description and from the accompanying drawings.

DETAILED DESCRIPTION

Figure 1:
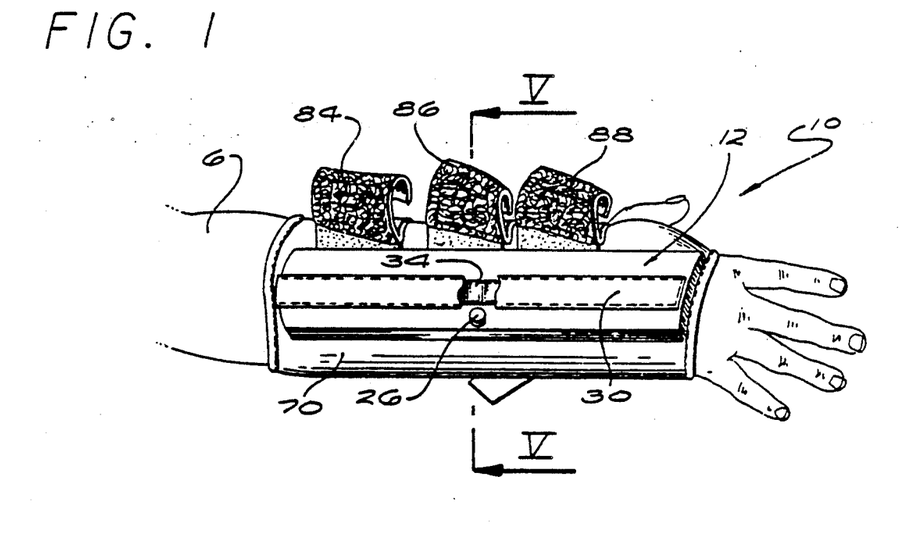
FIG. 1 is a perspective view of a soft good type cast illustrating the principles of the current invention in use on the right forearm.
Figure 2:
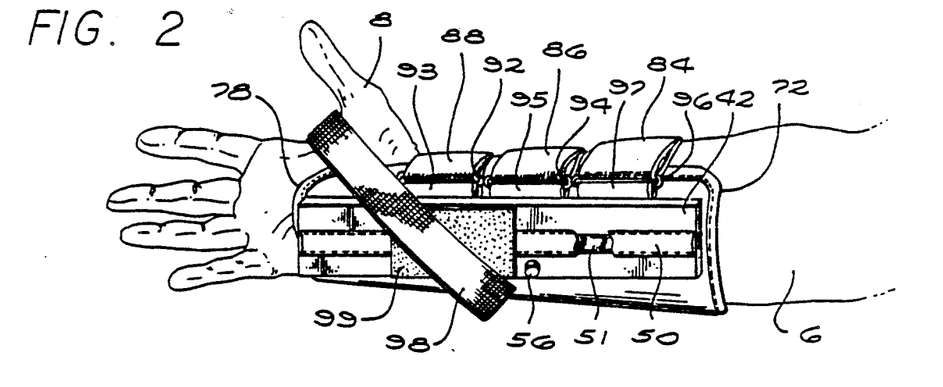
FIG. 2 is a perspective view of the orthopedic cast as seen from the inside of the right forearm.

Referring more particularly to the drawings, FIGS. 1 and 2 show the orthopedic cast 10 as it is used to immobilize the right forearm 6. FIG. 1 shows the back of the right forearm in a perspective view, with the cast 10 being mounted in place. In particular, it shows the pouch 12 wherein there is contained a water-activated hardenable urethane impregnated matrix. Water may be injected into the pouch through water inlet 26. The water activates the urethane polymer, which causes the elongated pouch to harden and conform to the shape of an individual's body limb upon the completion of the chemical reaction within pouch 12. Through the use of Velcro-covered straps 84,86,88, the cast 10 is firmly secured around the limb so that upon the introduction of water, the activated polymer hardens and takes a form or set providing a splint that conforms to the configuration of an individual's limb therein constrained.

Shown in FIG. 1 is splint rib assembly 30, which adds stability and can additionally be formed to the configuration of the arm and assist in the immobilization of the limb; and is particularly useful when the forearm is being initially set prior to the hardening of the urethane material. The splint rib assembly 30 can be a single splint rib 34 or a plurality of splint ribs. The splint rib 34 may be formed of a bendable strip of aluminum or a plastic strip having similar properties.

Figure 3:
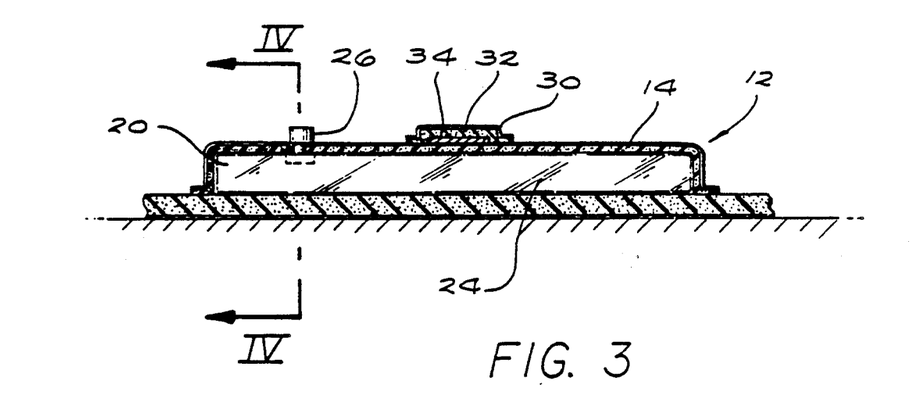
FIG. 3 is a cross-sectional view through an elongated pouch containing water activated hardenable material, and included in the soft goods type cast of FIGS. 1 and 2.
Figure 4:
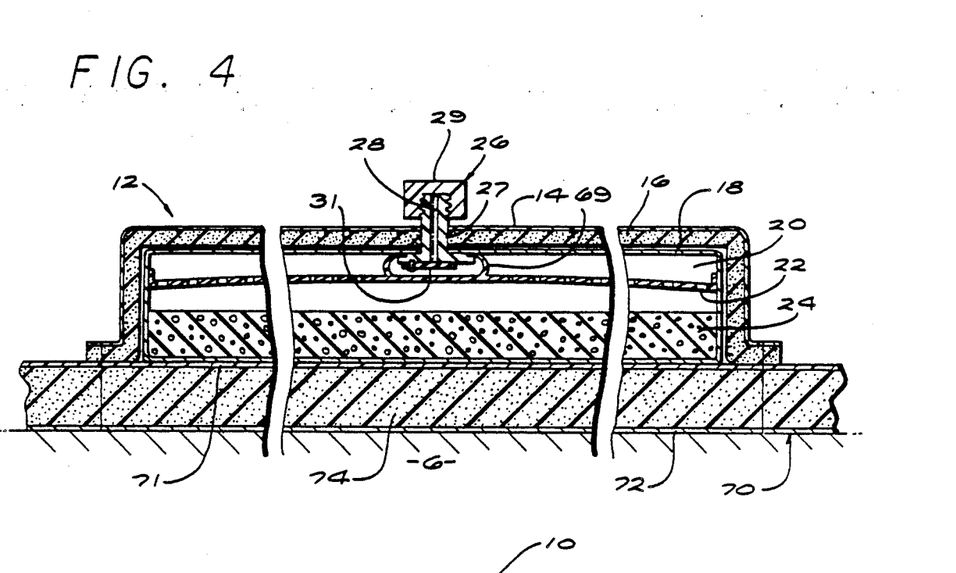
FIG. 4 is a cross-section through plane IV of FIG. 3, with a detailed showing of the pouch configuration.

FIG. 2 is a view of the cast 10 as seen from the inside of forearm 6. The cast 10 has two airtight pouches, 12 and 42, containing substrates or matrices 24 (as shown in FIGS. 3 and 4), impregnated with water-activatable urethane chemistry, or other hardenable material. The inside forearm pouch 42 has a splint rib assembly 50, having a configuration which is substantially the same as the splint rib assembly 30 noted on the front forearm pouch 12, shown in FIG. 1, a water entry port 56 through which water is injected into the foil and plastic pouch 42 to activate the urethane polymer and a Velcro attachment pad 99.

For further immobilization, the strap 98 having Velcro attached thereto is swung through the hand 8 and attached to velcro pad 99. This further assists immobilization and securing of the soft goods splint in the desired position on the forearm. As shown in FIG. 2, there are hinged or pivotally mounted metal loops 92, 94, 96 through which the straps 84, 86, 88 loop to adjustably secure the cast circumscribably to the limb. The metal loops 92, 94, 96 are attached to the cast assembly by fabric loops 93, 95, 97. The cast body as indicated by reference numeral 70 in FIG. 1 is lined with foam material for comfort, and the unit is stitched closed around its circumferal edges with beads of fabric as indicated at reference numerals 76 and 78 in FIG. 2.

FIG. 3 shows a cross-section of the pouch 12 from an orientation perpendicular to the arm 6 and shows the aluminum splint rib 34 covered with vinyl covering and padding 32. The covering could also be a sheet of vinyl or other tear resistant fabric without any padding. The elongated pouch 12 has an outside covering of vinyl 14 which is impervious to water. Water is injected into the interior 20 of the pouch 12 through input port 26 to activate the water-activated urethane hardenable polymer so that the resultant splint conforms to the configuration of the limb to which it is applied.

FIG. 4 shows a detailed cross-section through Plane IV of the pouch of FIG. 3. The pouch 12 contains the substrate or matrix 24 impregnated with the water-activated urethane polymer. The pouch in which the impregnated substrate or matrix is enclosed, is mounted on the outer surface 71 of the cast sleeve 70. The interior of the pouch 20 contains substrate or matrix 24 impregnated with water-activated urethane polymer, and a substantially parallel apertured plastic sheet 22 which delivers a uniform water flow to activate the urethane polymer impregnated into matrix 24.

Inlet 26 has a removable cap 29 attachable to stem 27, with a water entry canal 28 contained therein. Optional one-way valving action may be provided by plastic flap 31. A water injecting means such as a syringe, is coupled to water canal 28 through which a pre-determined fixed quantity of water is injected, so that the water comes into contact with, and is distributed by, apertured plastic sheet 22. The predetermined quantity of water could be supplied by a syringe which would inject the requisite water into the pouch. Sheet 22 runs generally parallel to the surface of matrix 24. It is desirable that water applied to inlet port 26 be uniformly applied to the matrix 24 to activate and harden the entire urethane impregnation. To facilitate this action, the plastic sheet material 22, which need only be a few thousandths of an inch thick, may be slightly further from matrix 24 adjacent inlet port 26, and may have fewer and smaller holes near the port 26 than at the two remote ends of the pouch. The sheet plastic element 69 may block direct flow of water through sheet 22 and may also hold the adjacent portion of sheet 22 further away from matrix 24. Substrate or matrix 24 can be impregnated open cell foam, fiberglass, or any other suitable carrier material for the urethane polymer. A honeycomb structure or a matrix of Kevlar or other high strength fibers of the types used in sports gear, could also be employed, impregnated with water-activated hardenable material, and having an open configuration to receive the water for activation.

The pouch 12 is mounted on the surface 71 of the sleeve 70, on a surface opposite to that which contacts the surface of the limb. The pouch 12 has a surface of vinyl 14 which is impervious to water. Beneath that is padding 16, and beneath the layer of padding 16 is a composite layer 18 which may be formed of several layers of foil and plastic alternated with one another, which is impervious to water and which completely encapsulates the interior 20. The composite layer 18 is airtight. Underneath composite layer 18 is a thin perforated plastic sheet 22. Typically the foil included in layer 18 will be made out of metals which are non-reactive to the urethane chemical reactions. The pouch 12 is mounted on a fabric or plastic surface 71, for example vinyl or brushed nylon, which has padding 74 and which may have a thin tricot material layer 72 which engages the skin of the limb 6. This material will allow a certain amount of air to flow to the skin, and the tricot is soft to the touch. Between tricot surface 72 and foam 74 can be an additional layer of insulating material (not shown) to further protect the limb from any heat of reaction that could occur by the introduction of water into the foil pouch 12. While small pouches such as those that are used with an arm cast would normally not have a problem with heat reaction, some of the large embodiments such as that indicated in FIG. 6, for use on a leg, may generate sufficient heat which could cause discomfort to the wearer. In such cases, a protective insulated layer may be appropriate.

Figure 5:
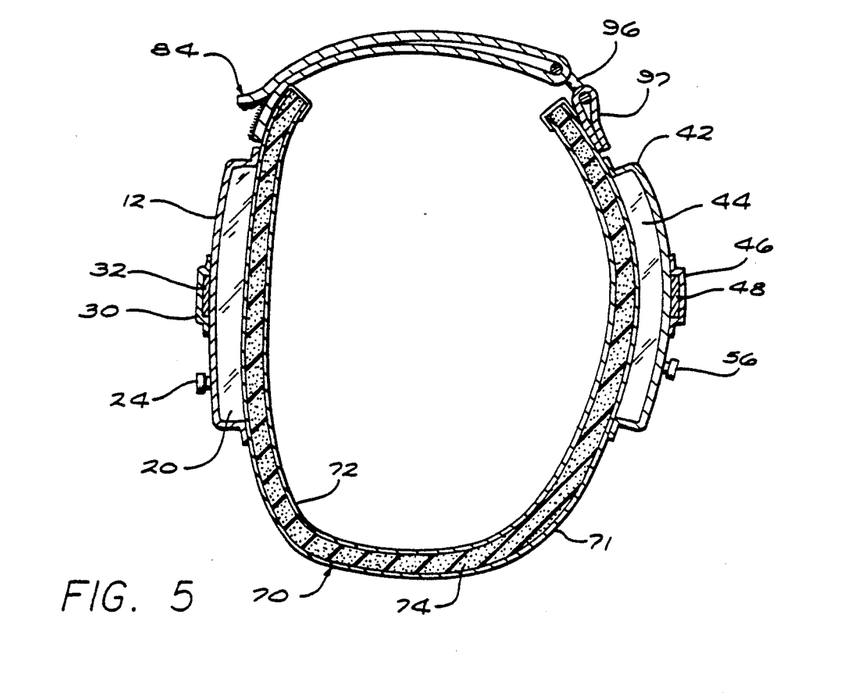
FIG. 5 is a view of the orthopedic cast in cross-section as it would appear on the right forearm.

FIG. 5 shows a cross-section of the soft goods cast as it would appear on the right forearm 6. The cross-sectional view shows two pouches 12 and 42 sitting approximately parallel to each other on the arm. FIG. 5 shows how the cast 10 takes the shape of the arm. Securing strap 84 loops through the strapping hinge loop 96. Cast 10 with exterior 71 which is made of vinyl or other water impervious material, padding 74, and interior 72, can be removed and replaced onto the arm to permit washing of the arm, and can be adjusted in size to accommodate changes in the arm involving reduction in swelling or slight muscle atrophy, for example.

Aluminum or bendable plastic splint ribs 32 and 48 can be made removable or permanent within the cast assembly. Additional rib members could be introduced on top of pouch 12 as well within the body of the cast 10 in areas below the foil pouches or in an area opposite to the velcro strapping within the padding area 74. In alternative embodiments, additional ribs can be added or removed depending on the severity of the injury to the limb or to obtain a desired degree of immobilization and stability. The splint ribs 32 and 48 are particularly helpful prior to water activation of the major splinting members in the pouch or pouches.

Figures 6, 7, 8, 9:
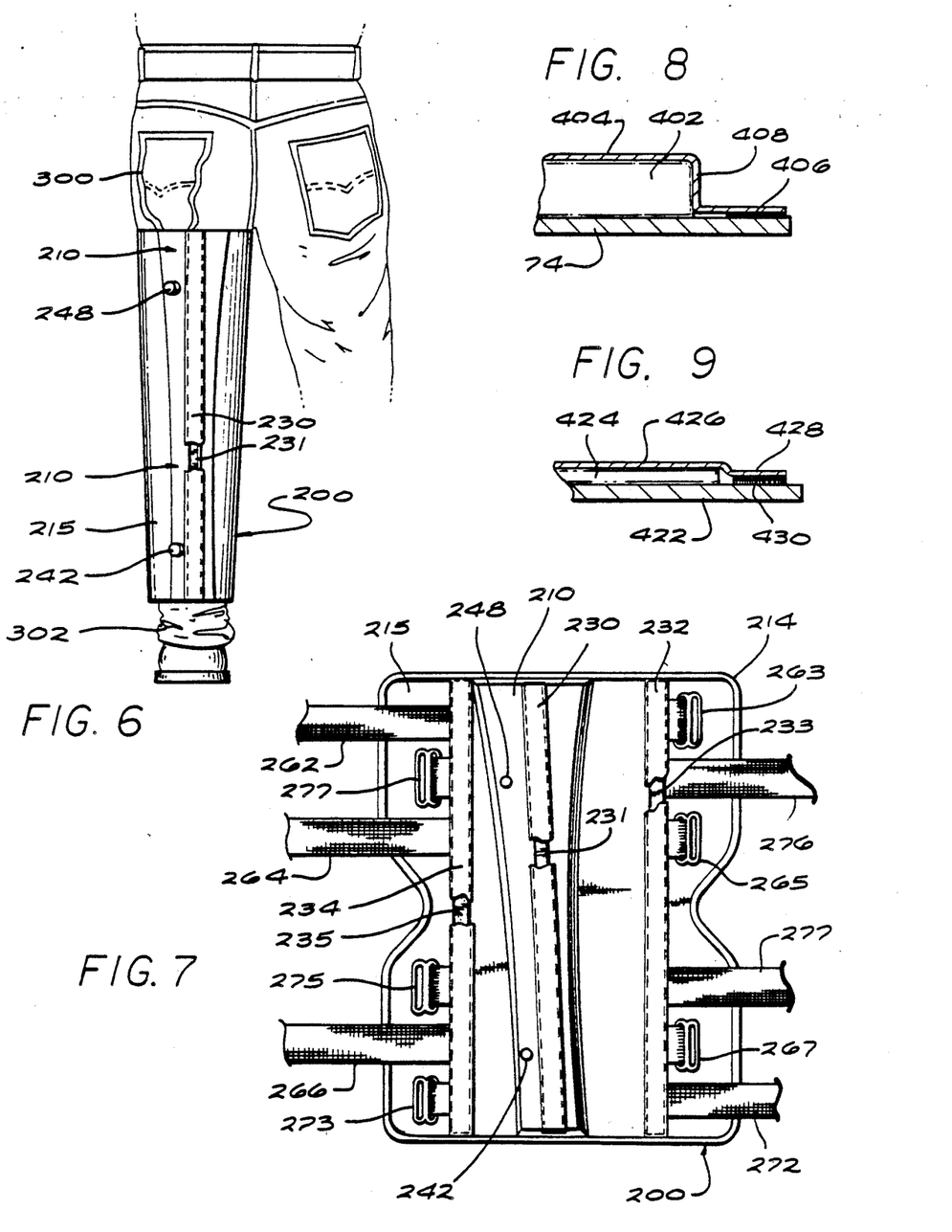
FIG. 6 illustrates an embodiment of the invention used on the left leg.
FIG. 7 is a detailed drawing of the soft goods cast of FIG. 6 shown in its unfolded configuration.
FIGS. 8 and 9 are cross-sectional views showing the removable nature of the splinting members.

FIG. 6 illustrates the principles of the invention in use on the left leg. It runs from the ankle portion 302 to just below the left buttock at 300. Obviously, the cast itself will be much larger than that shown in FIGS. 1-5, and utilizes one long continuous pouch 210 which will have two entry ports 242 and 248 for the introduction of water, or there could be a plurality of individual smaller foil plastic pouches. A predetermined quantity of water is injected into water ports 242 and 248 of the pouch 210. Pouch 210 encapsulates a urethane impregnated substrate or matrix as noted above. For stability and immobilization, before activation of the water hardening material, there can be a single aluminum splint rib 231 which runs along the surface of the foil plastic pouch 210, or a plurality of aluminum splint ribs could be employed. The nature of the injury and constraint desired would determine the number of splint ribs.

The cast 200 is shown in more detail in FIG. 7, where it is shown in a flattened or unwrapped configuration. The strapping means shown could be secured by various means such as velcro, buckles, hooks, tying or any means to secure the cast around a limb. The number of securing belts utilized on cast 200 is indicated by strapping 262, 264, 266, 272, 274, 276 which have mating attaching metal loops 277, 275, 273, 267, 265, 263 where each is located opposite to the other. The number of securing straps can vary depending on the size of the limb or the degree of immobilization and stability desired or required. As noted previously, additional aluminum or plastic splint ribs can be introduced as shown in FIG. 7. Splint ribs 233, 231, 235, with mating vinyl pockets or padding which cover the splint ribs, can be added as needed. In the embodiment here shown, the splint ribs 231, 233, 235, and pouch 210 are permanent. In other instances, these ribs and the hardened urethane splint and pouch assemblies can be removable, as discussed below. The foil plastic pouch 210 has two water entry ports or valves 248 and 242 into which pre-determined amounts of water are injected for activation of the water-activated urethane, as noted above. The cast surface 215 on which the foil plastic pouch is mounted, can be of a waterproof material, typically of vinyl, or any other water impervious material. Underneath, the construction would be the same as shown above, with foam padding, tricot material, and with a stitched nylon lip 214 around the edge. The cast 200 has a cut-out to conform to the knee of the individual. Obviously, the cast will come in various sizes and have the necessary cut-outs for each limb or joint configuration. Also, the casts for legs, ankles, wrists, and the like will vary according to a person's size and age.

FIGS. 8 and 9 showed alternative arrangements at the ends of the splinting elements, so that they are removable. More specifically, with reference to FIG. 8, the padded base layer 74 has the airtight pouch assembly 402 mounted thereon, and secured in place by the outer elongated enclosing sleeve 404. At one end of the pouch 402, which becomes a splint when activated, the material of the sleeve 404 is removably secured to the base layer 74 by matching Velcro pads 406 which are on the inner surface of the end closure 408 of sleeve 404, and on the outer surface of base layer 74. Accordingly, if it is desired to change the splint configuration, due to a reduction in swelling of the limb, or for other medical reasons, the hardened splint pouch 402 may be removed, and a new one reinserted. For use with this type of removable pouch, an inlet port would be provided, which could be flush with the surface of the pouch for ease of insertion.

FIG. 9 shows a similar alternative arrangement for splinting stays, such as those shown at 233 and 235 in FIG. 7. More particularly, an underlying base member 422 may have an aluminum or bendable plastic splinting stay 424 secured to it by the flexible sleeve 426. The end closure 428 may be removably secured to the base member 422 by matching Velcro pads 430 so that the splinting stay 424 may be removed.

Thus, as indicated in FIGS. 8 and 9, the cast units of FIGS. 1-7 may be modified and adapted to different needs and conditions by selective removal and replacement of the splinting elements, either for the same patient and condition, or for different patients.

Incidentally, regarding the nature of the water hardenable material, it may be a urethane type material as described in U.S. Pat. Nos. 4,376,438; 4,433,680; 4,442,833; 4,502,479 and 4,683,877. It is available from W. R. Grace under their identification FHP2000. Other water hardenable materials could also be used.

Figure 10:
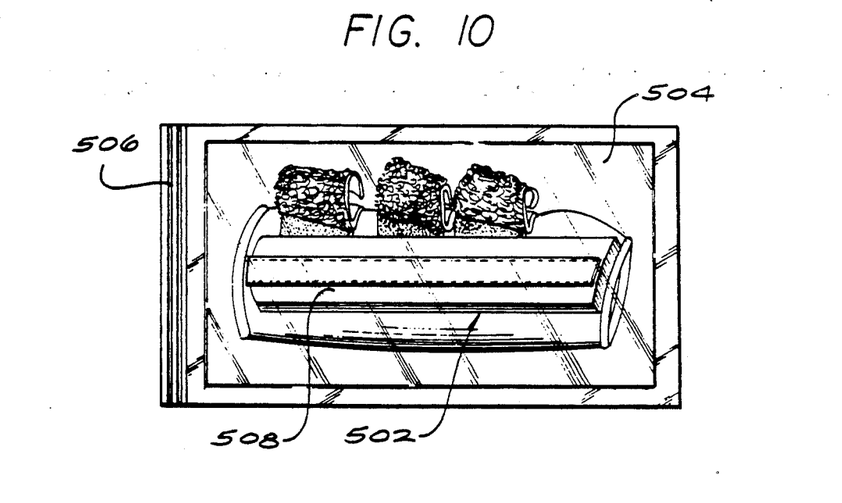
FIG. 10 shows a soft-goods type, formable orthopaedic cast, illustrating the principles of the invention, sealed within an air-tight, water and moisture proof bag.

Referring now to FIG. 10 of the drawings, it shows a soft-goods type orthopaedic cast 502 of the type shown in FIGS. 1-5 of the drawings, but with certain differences as will be discussed hereinbelow. In addition, the cast assembly 502 is sealed within a pouch 504 which is impermeable to both air and moisture. The pouch 504 may be formed of a combination of plastic and metal foil of the type discussed hereinabove, or may be of other known forms of flexible material which are impermeable to both air and moisture, including certain known transparent, flexible plastic material. Assuming that the pouch 504 is initially in the form of a bag, it may have the soft-goods type cast 502 slid into it, and may then be heat-sealed, or otherwise sealed along its left-hand edge 506, as indicated in FIG. 10.

In connection with earlier embodiments of the invention disclosed herein, for example the arrangements of FIGS. 1 through 5, it was noted that the water-activated, hardenable material was in an inner pouch formed of suitable airtight and moisture impermeable material, so that it would not be activated in the event the cast should become damp through high humidity or other factors involving the application of moisture to the unit. Further, in connection with the device of FIGS. 1 through 5, for example, water was added by injecting it through an input opening. In connection with the arrangements of FIG. 10 and certain other embodiments to be disclosed herein, an outer moisture impermeable bag 504 may be employed, and the inner water-activated, hardenable material may be activated in another manner. Thus, by having the material enclosing the water-activatable, hardenable material of porous material, for example, the unit may be activated by immersing the entire soft-goods type cast in water, and then applying it to the patient. Or alternatively, the unit may be secured onto the patient by the straps, and subsequently moistened by applying a water spray to the assembly, or, where appropriate, immersing the limb in water, to wet the inner water-activatable material.

Figure 11:
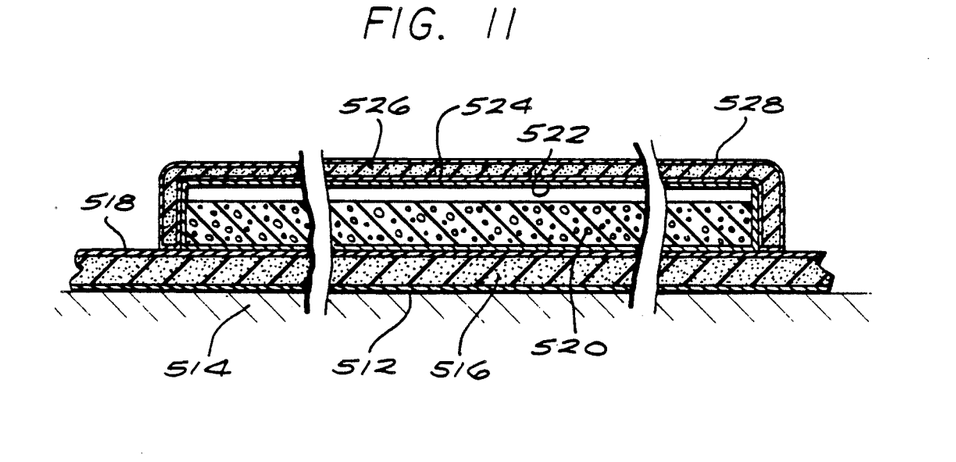
FIG. 11 is a cross-sectional view through an alternative embodiment of the invention.

FIG. 11 shows one alternative arrangement for implementing the splinting portion 508 of the soft-goods type cast assembly, as shown in FIG. 10. For simplicity, in FIG. 11 the outer bendable aluminum strip is not shown. More specifically, with reference to FIG. 11, the inner tricot material 512 would be provided to engage the skin of the limb 514 or other portion of the anatomy to which the cast is being applied. A thin layer of foam 516 is next to the tricot, and a layer of brushed nylon material 518 forms the outer surface of the soft-goods cast assembly. The hardenable material, such as urethane, is impregnated into open cell foam, or a fiberglass laminate, designated by the reference numeral 520. In addition, the material 520 containing the water-activatable, hardenable material may include one or more layers of composite material, such as KEVLAR, to provide additional strength. A space 522 is provided immediately above the material 520 to permit easy flow and access of water, to be later applied to the unit. The fabric enclosure 524 may be of any suitable water pervious material, such as brushed nylon. An additional thin layer of open cell foam 526 may then be covered with a layer of water permeable brushed nylon 528.

In practice, then, when it is desired to use the soft-goods type cast assembly of FIGS. 10 and 11, the impermeable outer pouch 504 is opened, the soft-goods assembly is applied to the forearm, which has been previously set or reduced, and water is applied to the material by having it flow through the permeable layers 524, 526, and 528. Following a fairly short period of time after the material 520 is exposed to moisture, it will polymerize and harden.

Incidentally, in the foregoing discussion of FIGS. 10 and 11, it was suggested that, when an outer pouch, such as that shown in FIG. 10 at reference numeral 504, is used, one need not use the inner impermeable pouch, as discussed in connection with FIGS. 1 through 5. However, in order to improve shelf life of the product, and to avoid any possibility that moisture would reach the hardenable material, a device of the type shown in FIGS. 1 through 5 could be packaged within an outer pouch, such as that shown in FIG. 10.

Figure 12:
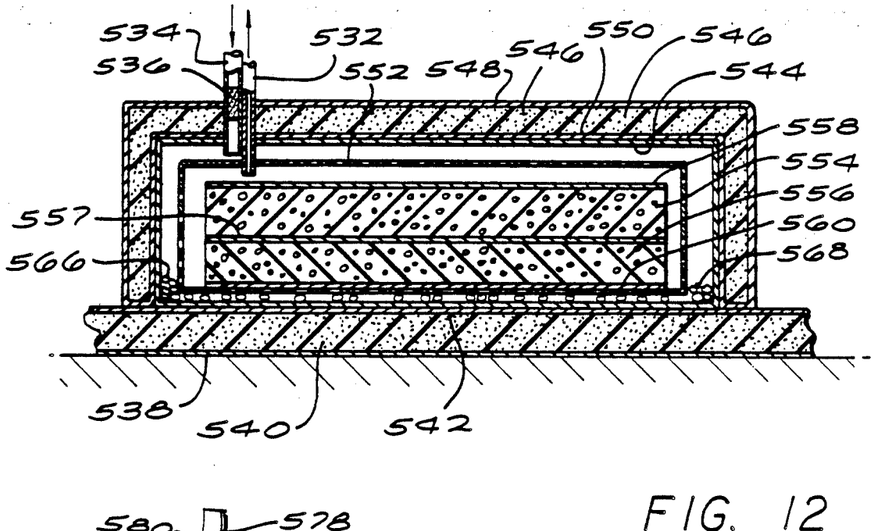
FIG. 12 is a partial cross-sectional view through another alternative embodiment of the invention.

Referring now to FIG. 12 of the drawings, it includes at least two important features, specifically the inclusion of a vent tube 532, in addition to the inlet tube 534. Also, some of the key chemical materials employed in the hardening step are mounted at reference numeral 536 in a capsule in the inlet tube 534. The capsule has a water-soluble coating, formed of polyvinyl alcohol, gelatin, or the like, so that when water is applied to the inlet tube 536, the wall of the capsule will immediately dissolve, and the chemical material within the capsule 536 will flow inwardly with the water to assist in the hardening of the water-hardenable material. The capsule 536 may completely fill the inlet tube, or may permit some initial flow of water past the capsule, as desired.

Other components shown in FIG. 12 are similar to materials previously discussed. More specifically, in FIG. 12 an inner layer of tricot material 538 is provided with an inner thin layer of foam 540 having a layer of brushed nylon 542 on its outer surface. Enclosed within an impermeable pouch 544 is an assembly including the water-hardenable activatable material to be discussed in greater detail hereinbelow. Enclosing the pouch 544 is a layer of foam material 546 sandwiched between two layers of brushed nylon 548 and 550.

Now, turning to the contents of the inner impermeable pouch 544, it includes an inner perforated pouch 552 which serves to facilitate and insure that water and, in some cases chemicals, supplied through the inlet tube 534 will be uniformly distributed around the surface of the two layers 554 and 556 of porous material impregnated with the water hardenable chemistry to be discussed hereinbelow. The porous material 554 and 556 may be open-celled foam material or may involve layers or fiberglass or other material. The upper and lower layers 558 and 560 may be formed of fiberglass, KEVLAR, or other high strength, knitted or woven fabrics, to provide increased strength to the overall assembly, following hardening of the material included in the layers 554 and 556. The central layer 562 may be formed of a material having a high affinity for water, so that water supplied through the inlet tube 534 and which is fed into the inner permeable pack, will be drawn to the inner surfaces of the layers 554 and 556. This material 556, additional quantities of which may be provided at 566 and 568, may be formed of hydrogel, or other similar materials such as modified starch, sold under the trademark "Super-Slurper".

In operation, therefore, when water is supplied through the inlet channel 534, the capsule 536 has its outer shell immediately dissolved so that the water and chemistry flows into the space between the walls of the impermeable pouch 554, and the perforated pouch 552. A flow path is provided completely around the layers 554, 556, 558, 560, so that these layers are thoroughly saturated with water, and the activation, hardening, and polymerization steps proceed rapidly. The vent tube 532, which has supplemental apertures between the two inner pouches 544 and 552, permits excess gas or air to flow out from the inner area, to permit full inward flow of the water and chemicals. The hydrogel or other similar substance at locations 566 and 568, serves to absorb excess water.

Figure 13:
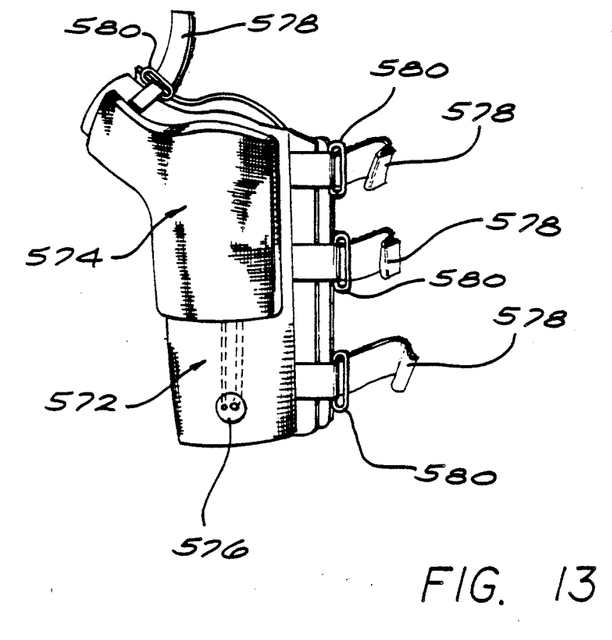
FIGS. 13–15 are various views of a soft-goods type orthopaedic cast for the thumb.
Figure 14:
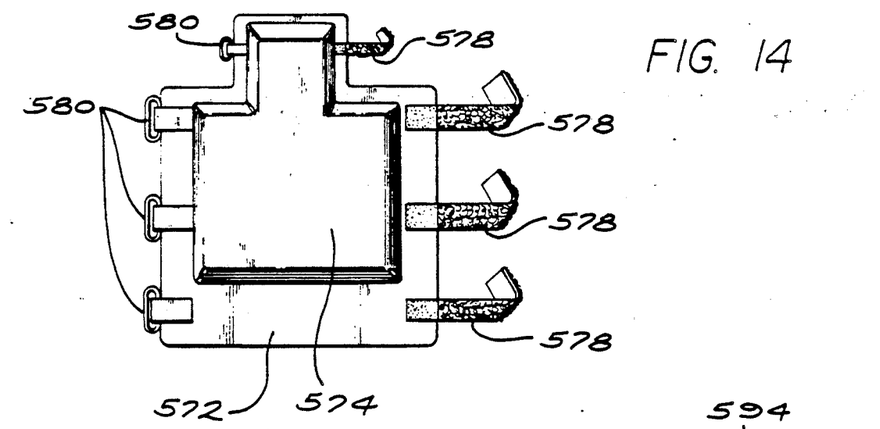
Figure 15:
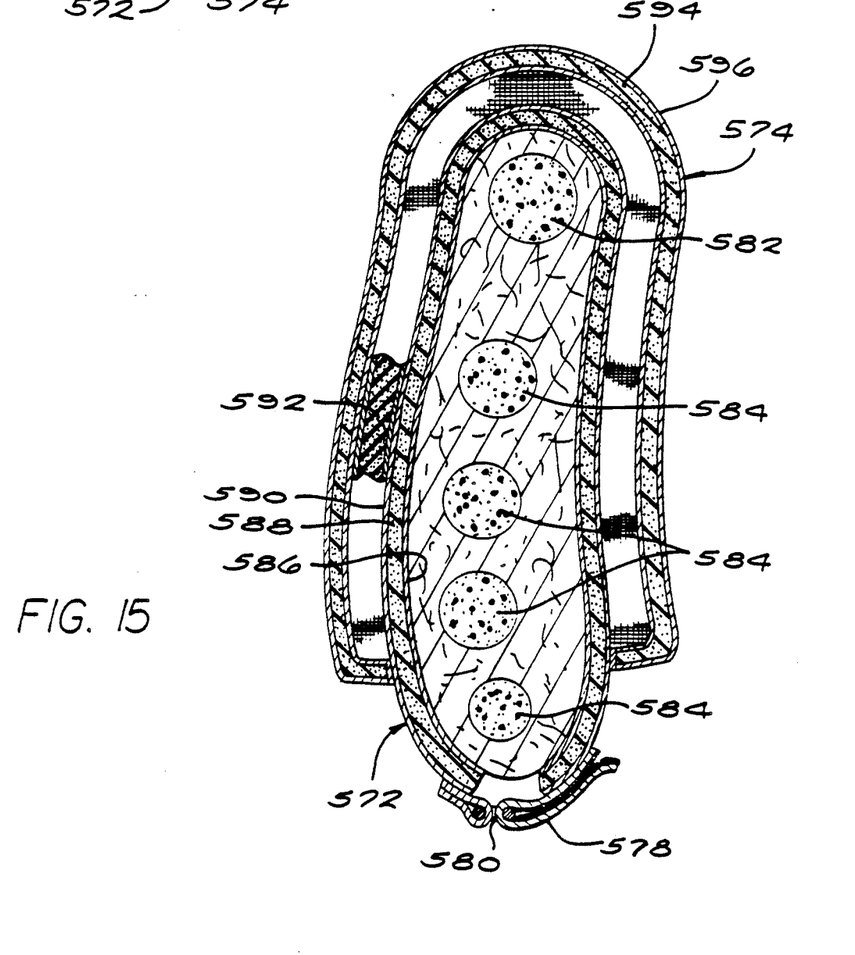

Turning now to FIGS. 13, 14 and 15, these are three views of an alternative soft-goods type formable cast, for the thumb. FIG. 13 is a side view of the unit; FIG. 14 is a view of the unit in its unfolded configuration; and FIG. 15 is a schematic cross-sectional view showing the assembly as it would appear when mounted on a person's hand, to immobilize and provide splinting for a broken thumb bone. With reference to FIG. 13, it includes a casing 572, and a pouch 574 for containing the hardenable urethane or other similar material. The unit may be either of the type shown and described hereinabove in connection with FIG. 11, or of the type shown in FIG. 12, in which inlet and vent tubes are provided, as indicated at coupling 576. The unit is held onto the hand, by suitable straps 578, which cooperate with metal loops 580, and which have Velcro material on their surfaces, as discussed hereinabove in connection with FIGS. 1 through 5 of the drawings.

FIG. 14 shows the soft-goods type cast of FIG. 13 in the unfolded configuration. It includes the raised area 574 containing the hardenable chemicals, mounted on the casing 572. The straps 578 and the metal loops 580 also appear in FIG. 14.

FIG. 15 is a schematic cross-sectional view through the hand and the base of the thumb bone 582, indicating generally the configuration of the soft-goods assembly when it is mounted on the hand in its splinting configuration for the thumb. In FIG. 15, the thumb bone is indicated by reference numeral 582, and the remaining bones of the hand are designated by the reference numeral 584. An inner layer of tricot 586 is followed by an adjacent thin layer of foam 588 which is covered by the brushed nylon layer 590. The other major components include the important middle layer of open-cell foam or fiberglass 592 into which the chemistry is impregnated, and the outer layer of foam 594, with a thin brushed nylon layer 596 covering the entire assembly. Other layers and components may be provided as discussed hereinabove in connection with FIGS. 11 and 12 of the drawings. It is particularly to be noted that the entire layered assembly 574, as shown in FIG. 15, is somewhat thicker than it would be in actual practice, in order to bring out the presence of the various layers discussed hereinabove. At the bottom of the figure are shown one of the straps 578, and one of the metal loops 580 which serve to hold the assembly together on a patient's hand. Incidentally, to accommodate variations in swelling, or to remove the cast for cleaning under controlled conditions following initial mending of the thumb bone, the assembly will flex somewhat about the curved portion of the "U-shaped" configuration. This will be true even after polymerization of the hardenable material.

Figures 16, 17:
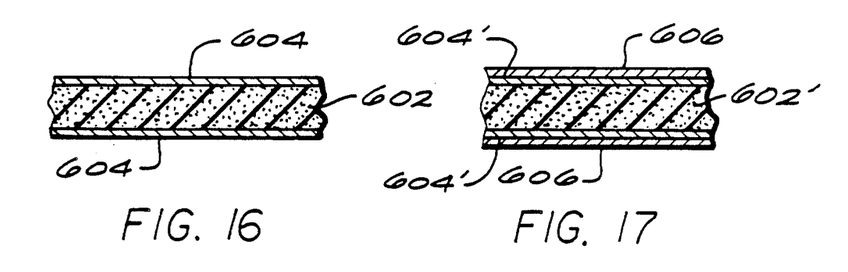

FIG. 16 shows one alternative arrangement for the inner portion of the soft-goods type activatable cast, in which open cell foam or fiberglass layers 602 have open weave layers 604 of Kevlar on either side thereof. With the high tensile strength of the Kevlar, and the hardened, polymerized materials in the open cell material 602, a strong splint results.

FIG. 17 shows a further embodiment in which the open cell or fiberglass-type material 602' is bounded by layers of Kevlar or similar material designated by reference numeral 604', and layers 606 of hydrogel, or "Super Slurper" material are located above and below the Kevlar layers, so that water is drawn to the vicinity of both surfaces of the laminate including layers 602' and 604'.

With regard to the chemical materials which may be employed in the implementation of the present invention, reference has been made to several patents which disclose materials which may be employed. In the present case, in connection with the embodiment of FIG. 12, for example, certain chemicals or pre-polymers are initially impregnated into the open cell material 554 and 556, and upon the introduction of the additional chemical included in the capsule 536, together with water, hardening or activation occurs as a result of polymerization. This action may be considered to be a result of the curing action of the additional chemicals which are supplied, in the water solution, and these additional materials may be either co-reactants or catalytic in their mode of operation.

Various systems may be employed; one such system employs a polyisocyanate as the pre-polymer, and amines as the co-reactant which may be housed in the inlet tubing in a PVA capsule to be added as the water is supplied to the inner pouch. The reaction between isocyanate and the amines is discussed at page 29 et seq: of a text entitled, "Plastics, Chemistry, and Technology", by Walter E. Driver, an Ostrand Rheinhold Company, New York, N.Y., copyright 1979. With regard to the application of the system to the arrangement of FIG. 12, the following steps may be employed. First, five grams of isocyanate 143L, (Upjohn) may be mixed with five grams of pluracol P710 (BASF) and this mixture may be further mixed with ten grams of Hypol FHP 5000 (W. R. Grace). One-half gram of benzoyl chloride (Fisher) may be added as a stabilizer, if desired. The foregoing may be impregnated into open cell foam laminate, three inches by ten inches by one-quarter inch thick. Included in the capsule in the inlet is two grams of tributyl-amine, and if desired, 0.25 grams Niax A-1 (Union Carbide) which acts as an accelerator. The Niax A-1 is understood to be a morpholine catalyst. When the inlet water brings the amines into contact with the isocyanates, in solution, polymerization occurs and the resultant long chains or polymers cause hardening of the impregnated open cell foam. When an inlet capsule is not employed, the amines are impregnated along with the pre-polymer isocyanate and no reaction occurs until the water is added, to permit reaction in the resulting solution.

It is noted that the isocyanate designated 143L from Upjohn has a relatively low viscosity, about 30 centipoise, and is therefore quite watery in its flow consistency. It is about 20%–30% isocyanate and has an equivalent weight of about 100–200, indicating that the content involves relatively short molecules. On the other hand, the Hypol from W. R. Grace has an isocyanate content of about 2% to 3%, an equivalent weight of 400–500, and a viscosity of about 10,000 to 20,000 centipoise, about like honey or corn syrup. It is also noted that the Hypol is a hydrophilic polymer and tends to foam when water is added, giving off carbon dioxide as curing is initiated.

The product resulting from the use of the two pre-polymer isocyanates of significantly different properties produces a product which sets up fairly quickly, within five or ten minutes, has high strength, and no significant objectionable odors. These properties are significantly superior to those of either of the two isocyanates alone and to many other pre-polymers which were tested.

Another system which may be employed involves the use of bisphenol epoxy resin with a hardener of diethylene triamine being supplied in the capsule in the inlet channel.

In accordance with a third system, a styrene unsaturated polyester, available from Dow, in the form of a vinyl ester is employed to impregnate the open cell foam, and in the capsule is peroxide, such as cumene hydroperoxide, or benzoyl peroxide.

The material for absorbing excess water following reaction could include polyvinyl alcohol in powder, beads, or sheet form, modified cellulose, available in powder, beads or sheet form, dehydrated hydrogel, or other known materials which have an affinity for water.

It is to be understood that the foregoing description of the accompanying drawings shall relate to preferred and illustrated embodiments of the invention. Various modifications may be employed without departing from the sphere and the scope of the invention. Thus, by way of example and not limitation, instead of using foil plastic pouches on the surface of the cast, they could be incorporated within the cast material between the surfaces 72 and 71. In addition, the various ribs as indicated above can be removable and constructed of bendable plastic, which is similar to aluminum in its mechanical properties. There can be many tie systems and many configurations for the cast. Instead of layers of foil and plastic, a single layer of an impervious flexible material could be employed in the construction of the pouches. The use of a flexible wide zipper would have a different configuration than that illustrated; and overlapping Velcro covered portions on the fabric of the body of the soft goods cast could be used to hold the unit in place. Also, the configuration of the cast for an elbow would be much different than for a leg or a section of an arm. In addition, the orthopedic cast's function should not be limited to humans, but can be utilized on animals such domestic animals as dogs and cats, and for the use with farm animals, such as horses, cows and so forth. The veterinary uses as well as the medical uses of the invention are self-evident and are not to be limited in any way to a suggested specific animal or human use. Concerning the encapsulation of activating material such as the amines, in addition to encapsulation in the inlet duct, the activating material may be in the form of small capsules with dissolvable coatings or membranes dispersed within or adjacent to the hardenable material. It is further noted that in some cases it may be desirable to use more than one inlet duct and/or more than one vent duct. Concerning the pouches, they could be made of the materials mentioned hereinabove, or alternatively, of fabric coated with plastic material to provide impermeability to gases and/or liquids, or any other impermeable flexible material. Also, when using arrangements as in FIG. 17, the structure may be simplified by dispensing with the perforated or permeable layer or pouch 552 as shown in FIG. 12. Further, the activatable, hardenable material, such as urethane, may be coated on one or more layers of a flexible material (permeable or impermeable) and arranged to receive activation by exposure to water and/or other activation materials. Concerning the embodiment of FIG. 11 one or all of the layers between the activatable material 520 and an outer layer 526 or 528 may be omitted, to simplify the structure. Accordingly, the present invention is not limited to the specific arrangements as shown in the drawings and described in the foregoing detailed description.

What is claimed is:

1. An orthopaedic soft-goods type cast assembly comprising:
    a flexible casing, for enclosing a limb or other portion of the anatomy, having a substantial extent and opposed edges;
    said casings being manufactured or initially formed or tailored specifically to fit a selected portion of the anatomy of a patient, and having an initial irregular contour or pattern which follows the irregular and unique shape of said selected portion of the anatomy;
    means for holding the two outer edges of said casing toward one another and securing said casing onto a limb or the like adjustably to accommodate variations in swelling;
    liquid or gas permeable material impregnated with an activatable, hardenable material which structurally conforms to said portion of the anatomy when activated, said permeable material being mounted to and secured to conform with the configuration of said casing;
    a gas and water impervious pouch for preventing premature activation of said hardenable material;
    means for activating said hardenable material to form a cast or a splint for the limb or other portion of the anatomy;
    said activatable material constituting a pre-polymer;
    means for polymerizing said activatable hardenable material;
    isolation means for enclosing said polymerizing means within a thin layer of water soluble material; and
    means for providing access to said isolation means and to said activatable hardenable material by water, whereby said isolation means is dissolved, and said polymerizing means and said water activates said hardenable material, causing polymerization thereof, and hardening.

2. An assembly as defined in claim 1 wherein said polymerizing means is located in a capsule having a water soluble outer layer, in an input duct for supplying water to said activatable hardenable material.

3. An assembly as defined in claim 1 wherein said polymerizing means is physically located adjacent said activatable, hardenable material but is separated therefrom by the water soluble isolation means.

4. An orthopaedic soft-goods type cast assembly as defined in claim 1 wherein straps are provided for securing the edges of said casing together.

5. An orthopaedic soft-goods type cast assembly as defined in claim 1 wherein said gas and water impervious pouch encloses the entire soft-goods cast assembly.

6. An orthopaedic soft-goods type cast assembly as defined in claim 1 wherein said gas and water impervious pouch is formed as a part of said assembly which directly encloses said impregnated liquid permeable assembly.

7. An orthopaedic soft-goods type cast assembly as defined in claim 1 including an inlet for supplying fluid to the impregnated liquid permeable material, and a vent outlet to permit the escape of air or other gases from the liquid permeable material so that the fluid may freely permeate the liquid permeable material.

8. An orthopaedic cast assembly as defined in claim 1 wherein said activating means includes an entry port on the outer surface of said assembly and means for directing water through said entry port to contact the contents of said pouch.

9. An orthopaedic soft goods type cast assembly as defined in claim 1 wherein said activatable, hardenable material is a urethane pre-polymer.

10. An orthopaedic soft-goods type cast assembly as defined in claim 1 wherein said activatable, hardenable material is made up of two isocyanate pre-polymers, one having a viscosity less than 500 centipoise and the other having a viscosity greater than 1,000 centipoise.

11. An orthopaedic soft-goods type cast assembly as defined in claim 1 wherein said activatable, hardenable material is made up of two isocyanate pre-polymers, one having a viscosity less than 200 centipoise and the other having a viscosity greater than 4,000 centipoise.

12. An orthopaedic soft-goods type cast assembly comprising:
- a flexible casing for enclosing a limb or other portion of the anatomy having a substantial extent and opposed edges;
- said casings being manufactured or initially formed or tailored specifically to fit a selected portion of the anatomy of a patient, and having an initial irregular contour or pattern which follows the irregular and unique shape of said selected portion of the anatomy;
- means for holding the two outer edges of said casing toward one another and securing said casing onto a limb or the like adjustably to accommodate variations in swelling;
- an activatable, hardenable material which structurally conforms to said limb when activated, said activatable, hardenable material being mounted to and secured to conform with the configuration of said casing;
- means for activating said hardenable material to form a cast or a splint for the limb or other portion of the anatomy;
- said activatable material constituting a pre-polymer;
- means for polymerizing said activatable hardenable material;
- isolation means for enclosing said polymerizing means within a thin layer of water soluble material; and
- means for providing access to said isolation means and to said activatable hardenable material by water, whereby said isolation means is dissolved, and said polymerizing means and said water activates said hardenable material, causing polymerization thereof, and hardening.

13. An assembly as defined in claim 12 wherein said polymerizing means is located in a capsule having a water soluble outer layer, in an input duct for supplying water to said activatable hardenable material.

14. An assembly as defined in claim 12 wherein said polymerizing means is physically located adjacent said activatable, hardenable material but is separated therefrom by the water soluble isolation means.

15. An orthopaedic soft-goods type cast assembly as defined in claim 12 further comprising a gas and moisture impervious pouch for preventing premature activation of said hardenable material.

16. An orthopaedic soft-goods type cast assembly as defined in claim 15 wherein said air and water impervious casing encloses the entire soft-goods cast assembly.

17. An orthopaedic soft-goods type cast assembly as defined in claim 15 wherein said gas and water impervious casing is a pouch which formed a part of said assembly and which directly encloses said impregnated liquid permeable assembly.

18. An orthopaedic soft-goods type cast assembly as defined in claim 12 wherein said activatable, hardenable material is made up of two isocyanate pre-polymers, one having a viscosity less than 500 centipoise and the other having a viscosity greater than 1,000 centipoise.

19. An orthopaedic soft-goods type cast assembly as defined in claim 12 wherein said activatable, hardenable material is made up of two isocyanate pre-polymers, one having a viscosity less than 200 centipoise and the other having a viscosity greater than 4,000 centipoise.

20. An orthopaedic soft-goods type cast assembly comprising:
- a flexible casing for enclosing a limb or other portion of the anatomy having a substantial extent and opposed edges;
- said casings being manufactured or initially formed or tailored specifically to fit a selected portion of the anatomy of a patient, and having an initial irregular contour or pattern which follows the irregular and unique shape of said selected portion of the anatomy;
- means for holding the two outer edges of said casing toward one another and securing said casing onto a limb or the like adjustably to accommodate variations in swelling;
- liquid or gas permeable material impregnated with an activatable, hardenable material which structurally conforms to said limb when activated, said liquid permeable material being mounted to and secured to conform with the configuration of said casing;
- means for activating said hardenable material to form a cast or a splint for the limb or other portion of the anatomy; and
- said assembly including an inlet for supplying activation to the impregnated liquid permeable material, and a vent outlet to permit the escape of air or other gases from the liquid or gas permeable material so that the fluid may freely permeate the liquid permeable material;
- said activatable material constituting a pre-polymer;
- means for polymerizing said activatable hardenable material;
- isolation means for enclosing said polymerizing means within a thin layer of water soluble material; and
- means for providing access to said isolation means and to said activatable hardenable material by water, whereby said isolation means is dissolved, and said polymerizing means and said water activates said hardenable material, causing polymerization thereof, and hardening.

21. An assembly as defined in claim 20 wherein said polymerizing means is located in a capsule having a water soluble outer layer, in an input duct for supplying water to said activatable hardenable material.

22. An assembly as defined in claim 20 wherein said polymerizing means is physically located adjacent said activatable, hardenable material but is separated therefrom by the water soluble isolation means.

23. An orthopaedic soft-goods type cast assembly comprising:
- a flexible casing, for enclosing a limb or other portion of the anatomy, having a substantial extent and opposed edges;
- means for holding the two outer edges of said casing toward one another and securing said casing onto a limb or the like adjustably to accommodate variations in swelling;
- liquid or gas permeable material impregnated with an activatable, hardenable material which structurally conforms to said portion of the anatomy when activated, said permeable material being mounted to and secured to conform with the configuration of said casing;
- a gas and water impervious pouch for preventing premature activation of said hardenable material;

means for activating said hardenable material to form a cast or a splint for the limb or other portion of the anatomy;

said activatable material constituting a pre-polymer;

means for polymerizing said activatable hardenable material;

isolation means for enclosing said polymerizing means within a thin layer of water soluble material; and means for providing access to said isolation means and to said activatable hardenable material by water, whereby said isolation means is dissolved, and said polymerizing means and said water activates said hardenable material, causing polymerization thereof, and hardening.

24. An orthopaedic soft-goods type cast assembly as defined in claim 23 wherein straps are provided for securing the edges of said casing together.

25. An orthopaedic soft-goods type cast assembly comprising:

a flexible casing, for enclosing a limb or other portion of the anatomy, having a substantial extent and opposed edges;

means for holding the two outer edges of said casing toward one another and securing said casing onto a limb or the like adjustably to accommodate variations in swelling;

liquid or gas permeable material impregnated with an activatable, hardenable material which structurally conforms to said portion of the anatomy when activated, said permeable material being mounted to and secured to conform with the configuration of said casing;

means for activating said hardenable material to form a cast or a splint for the limb or other portion of the anatomy;

means for polymerizing said activatable hardenable material; and said activatable, hardenable material being made up of two isocyanate pre-polymers, one having a viscosity less than 500 centipoise and the other having a viscosity greater than 1,000 centipoise.

26. An orthopaedic soft-goods type cast assembly as defined in claim 25 wherein said one isocyanate pre-polymer has a viscosity less than 200 centipoise, and said other isocyanate pre-polymer has a viscosity above 4,000 centipoise.

* * * * *